United States Patent
Puder et al.

(10) Patent No.: US 9,763,905 B2
(45) Date of Patent: Sep. 19, 2017

(54) THERAPEUTIC TARGET FOR THE TREATMENT OF CANCERS AND RELATED THERAPIES AND METHODS

(71) Applicant: CHILDREN'S MEDICAL CENTER CORPORATION, Boston, MA (US)

(72) Inventors: Mark Puder, Medfield, MA (US); Deepika Nehra, Boston, MA (US); Brian Kalish, Brookline, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/777,485

(22) PCT Filed: Mar. 17, 2014

(86) PCT No.: PCT/US2014/030646
§ 371 (c)(1),
(2) Date: Sep. 15, 2015

(87) PCT Pub. No.: WO2014/145817
PCT Pub. Date: Sep. 18, 2014

(65) Prior Publication Data
US 2016/0045468 A1    Feb. 18, 2016

Related U.S. Application Data

(60) Provisional application No. 61/800,680, filed on Mar. 15, 2013.

(51) Int. Cl.
*A61K 31/202* (2006.01)
*A61K 31/20* (2006.01)
*A61K 31/343* (2006.01)
*A61K 31/196* (2006.01)
*A61K 31/192* (2006.01)
*A61K 31/201* (2006.01)

(52) U.S. Cl.
CPC .......... *A61K 31/202* (2013.01); *A61K 31/192* (2013.01); *A61K 31/196* (2013.01); *A61K 31/20* (2013.01); *A61K 31/201* (2013.01); *A61K 31/343* (2013.01)

(58) Field of Classification Search
CPC .... A61K 31/20; A61K 31/201; A61K 31/202; A61K 31/192; A61K 31/196; A61K 31/343
See application file for complete search history.

(56) References Cited

U.S. PATENT DOCUMENTS

2007/0088076 A1    4/2007    Ojima

FOREIGN PATENT DOCUMENTS

WO    WO001/17524 A1 * 3/2001

OTHER PUBLICATIONS

Barnes et al. Pediatric Research, (2012), 71(2), 168-178.*
Han et al. Yakhak Hoechi, (2008), 52(4), 264-273, Abstract.*
Vucicevic et al. Autophagy, (2011), 7(1), 40-50.*
Gajewski et al. Book titled "Targeted Therapeutics in Melanoma" p. 139-140, published Dec. 14, 2011.*
Mundal et al Nature Chemistry 2, (2010), pp. 294-297.*
Sasaki, et al. J. Med. Chem., 2011, 54 (5), pp. 1365-1378.*
Kim, et al. "Fatty fish and fish omega-3 fatty acid intakes decrease the breast cancer risk: a case-control study." BMC Cancer 9:216; Abstract (2009).
Hawcroft, et al. "The omega-3 polyunsaturated fatty acid eicosapentaenoic acid inhibits mouse MC-26 colorectal cancer cell liver metastasis via inhibition of PGE2-dependent cell motility." Br JPharmacol. 166(5):1724-37; Abstract (2012).
Barnes, et al. "Inhibition of neuroblastoma cell proliferation with omega-3 fatty acids and treatment of a .murine model of human neuroblastoma using a diet enriched with omega-3 fatty acids in combination with sunitinib." Pediatr Res. 71 (2):168-78; p. 177, col. 1. (2012).
Bald, et al., "G protein-coupled receptors for energy metabolites as new therapeutic targets," Nat Rev Drug Discov. 11(8): Abstract (2012).
Hardy, et al., "Oleate Promotes the Proliferation of Breast Cancer Cells via the G Protein-coupled Receptor GPR40*," The Journal of Biological Chemistry vol. 280, No. 14, Issue of Apr. pp. 13285-13291 (2005).
Zajdel, et al., "Polyunsaturated Fatty Acids Inhibit Melanoma Cell Growth In Vitro," Acta Poloniae Pharmaceutica—Drug Research, vol. 70 No. 2 pp. 365-369, (2013).
Yonezawa, et al., "Existence of GPR40 functioning in a human breast cancer cell line, MCF-7," Biochemical and Biophysical Research Communications 314: 805-809 (2004).
Sun, et al., "Omega-3 fatty acids induce apoptosis in human breast cancer cells and mouse mammary tissue through syndecan-1 inhibition of the MEK-Erk pathway," Carcinogenesis vol. 32 No. 10 pp. 1518-1524 (2011.).
Feng, et al., "GPR40: A therapeutic target for mediating insulin secretion (Review)," International Journal of Molecular Medicine 30: 1261-1266 (2012).
International Search Report for International Application PCT/US2014/030646, dated Nov. 6, 2014.
Mikami, et al., "Discover of Phenylpropanoic Acid Derivatives Containing Polar Functionalities as Potent and Orally Bioavailable G Protein-Coupled Receptor 40 Agonists for the Treatment of Type 2 Diabetes," J. Med. Chem., 55:3756-3776, (2012).

* cited by examiner

*Primary Examiner* — Yong Chu
(74) *Attorney, Agent, or Firm* — Lisa M. Warren, Esq.; Morse, Barnes-Brown & Pendleton, P.C.

(57) ABSTRACT

Disclosed herein are compositions and methods for treating or preventing certain cancers in a subject. In certain embodiments such compositions and methods generally relate to the use of G-coupled protein receptor 40 (GPR40) agonists to inhibit the growth or induce apoptosis of certain cancer cells. The compositions and related methods disclosed herein may be used to treat subjects affected by cancers, such as melanoma, medullary thyroid carcinoma, malignant peripheral nerve sheath tumors and neuroblastoma, and to reduce the incidence of metastases in such affected subjects.

7 Claims, 8 Drawing Sheets

THERAPEUTIC TARGET FOR THE TREATMENT OF CANCERS AND RELATED THERAPIES AND METHODS

RELATED APPLICATIONS

This application is a national stage filing under 35 U.S.C. 371 of International Application No. PCT/US2014/030646, filed Mar. 17, 2014, which claims the benefit of U.S. Provisional Application No. 61/800,680, filed Mar. 15, 2013, the entire teachings of which are incorporated herein by reference. International Application PCT/US2014/030646 was published under PCT Article 21(2) in English.

GOVERNMENT SUPPORT

This invention was made with government support under award number T32DK007754-12 awarded by the National Institutes of Health. The government has certain rights in the invention.

BACKGROUND OF THE INVENTION

Cancer represents a major public health concern, and in the United States, one in four deaths is due to cancer (Siegel, et al., *CA Cancer J Olin.* 63, 11-30 (2013)). Melanoma is the deadliest form of skin cancer. The annual incidence of melanoma has increased by more than 60% over the last 3 decades, making it the most rapidly increasing of all cancers worldwide (Foundation, A. M. 2009 Skin Cancer Fact Sheet (2009)). While early stage cancers such as melanomas can be cured with surgical excision, the outcome for many patients with advanced stage cancer remains dismal, despite aggressive treatment. Current treatment strategies include high dose chemotherapy and immunotherapy, both of which are associated with significant, and often treatment-limiting, adverse effects.

Novel therapies are needed for treating cancer and for reducing cancer metastasis. In particular, there is great demand for safe and effective therapies that are capable of treating (e.g., reducing or improving symptoms of or curing) cancers, especially melanomas.

SUMMARY OF THE INVENTION

Disclosed herein are novel compositions and related methods that are useful for treating and preventing certain cancers (e.g., melanoma) and for reducing metastasis of such cancers. In particular, the inventions disclosed herein generally relate to the findings that modulating the G-coupled protein receptor 40 (GPR40) (e.g., by selective agonist stimulation) mediates inhibitory or cytotoxic effects on cancer cells, and that agonists of GPR40 (e.g., fatty acids) are capable of treating and/or preventing certain cancers (e.g., cancers derived from neural crest tissues).

In certain embodiments the inventions disclosed herein relate to methods of treating or preventing certain cancers (e.g., melanoma) in a subject (e.g., a mammal) affected by or at risk for such cancer, wherein such methods comprise a step of administering a composition to the subject and thereby treating or preventing the cancer, wherein the composition comprises an effective amount of a GPR40 agonist (e.g., polyunsaturated fatty acids, such as omega-3 fatty acids).

In certain embodiments, the cancer is derived from neural crest tissues (e.g., neuroblastoma and melanoma). For example, the cancer may include, but is not limited to, a neuroblastoma, ganglioneuroblastoma, melanoma, carcinoid tumor, medullary thyroid carcinoma, malignant peripheral nerve sheath tumors, pheochromocytoma and paraganglioma.

Also disclosed are methods of inhibiting metastasis of certain cancers (e.g., neuroblastoma and melanoma) in a subject, wherein such methods comprise a step of administering a composition to the subject (e.g., a human) and thereby inhibiting cancer metastasis, wherein the composition comprises an effective amount of a GPR40 agonist (e.g., an omega-3 fatty acid such as docosahexaenoic acid).

In some embodiments, disclosed herein are methods of inhibiting the growth of a cancer cell line (e.g., a melanoma cell line expressing GPR40), wherein such methods comprise a step of contacting such cancer cell line with a composition and thereby inhibiting the growth of the cancer cell line, wherein the composition comprises an effective amount of a GPR40 agonist (e.g., TAK-875).

In other embodiments, the present inventions relate to methods of inducing apoptosis of a cancer cell expressing GPR40 (e.g., melanoma, medullary thyroid carcinoma, malignant peripheral nerve sheath tumors or neuroblastoma cancer cells), wherein such methods comprise a step of contacting the cancer cell (e.g., a melanoma cell expressing GPR40) with a composition and thereby inducing apoptosis of the cancer cell, wherein the composition comprises an effective amount of a GPR40 agonist (e.g., an omega-3 fatty acid such as docosahexaenoic acid and/or eicosapentaenoic acid).

In certain embodiments, the compositions and methods disclosed herein may be used to treat or prevent certain cancers (e.g., cancers or tumors expressing GPR40). In some embodiments, the cancer is derived from neural crest tissues. For example, the cancer may be one or more of neuroblastoma, ganglioneuroblastoma, melanoma, carcinoid tumor, pheochromocytoma, medullary thyroid carcinoma, malignant peripheral nerve sheath tumors and paraganglioma.

Also disclosed herein are methods of treating or preventing melanoma in a subject (e.g., an adolescent or an adult human) affected by or at risk for melanoma, wherein such methods comprise a step of administering (e.g., topically or orally administering) a composition to the subject and thereby treating or preventing the melanoma, wherein the composition comprises an effective amount of one or more omega-3 fatty acids (e.g., one or more omega-3 fatty acids selected from the group consisting of alpha-linolenic acid, docosahexaenoic acid and eicosapentaenoic acid).

Also disclosed herein are methods of treating or preventing neuroblastoma in a subject (e.g., a pediatric subject) affected by or at risk for neuroblastoma, wherein such methods comprise a step of administering (e.g., administering orally or parenterally) a composition to the subject and thereby treating or preventing the neuroblastoma, wherein the composition comprises an effective amount of one or more omega-3 fatty acids (e.g., docosahexaenoic acid and/or eicosapentaenoic acid).

Also disclosed are methods of treating or preventing cancer (e.g., cancer derived from neural crest tissues) in a subject affected by or at risk for cancer, wherein the method comprises administering a composition to the subject and thereby treating or preventing the cancer, wherein the composition comprises an effective amount of TAK-875.

Also disclosed herein are methods of treating or preventing cancer by activating phospholipase C (e.g., by modulating GPR40 or by administering a GPR40 agonist). Also disclosed are methods of treating or preventing cancer by stimulating the production of inositol 1,4,5-triphosphate and diacylglycerol (e.g., by modulating GPR40 or by administering a GPR40 agonist). Also disclosed are methods of treating or preventing cancer by increasing levels of intracellular calcium to activate caspase-dependent apoptotic pathways (e.g., by modulating GPR40 or by administering a GPR40 agonist).

Each of the methods and compositions disclosed herein may be useful for the treatment of cancers. In certain embodiments, the cancer is selected from the group consisting of neuroblastoma, ganglioneuroblastoma, melanoma, carcinoid tumor, pheochromocytoma, medullary thyroid carcinoma, malignant peripheral nerve sheath tumors and paraganglioma. In other embodiments, the cancer is derived from neural crest tissues. In other embodiments, the cancer is melanoma. In other embodiments, the cancer is neuroblastoma. In other the cancer is medullary thyroid carcinoma. In other embodiments, the cancer is a malignant peripheral nerve sheath tumor. In other embodiments, the cancer cells or tumor cells express GPR40.

Each of the methods disclosed herein generally comprise an administering or contacting step involving a GPR40 agonist. In certain embodiments, the GPR40 agonist comprises one or more omega-3 fatty acids. For example, the one or more omega-3 fatty acids may be selected from the group consisting of eicosapentaenoic acid (EPA), docosahexaenoic acid (DHA) and alpha-linolenic acid (ALA). In certain embodiments of each method disclosed herein, the omega-3 fatty acid is docosahexaenoic acid (DHA). In some embodiments, the GPR40 agonist comprises a $C_8$-$C_{24}$ fatty acid. In some embodiments of the methods disclosed herein, the GPR40 agonist comprises an unsaturated fatty acid or polyunsaturated fatty acid (e.g., eicosapentaenoic acid (EPA), docosahexaenoic acid (DHA), alpha-linolenic acid (ALA) and combinations thereof). In some embodiments, such an unsaturated or polyunsaturated fatty acid is an omega-3 fatty acid. In other embodiments of the methods disclosed herein, the fatty acid is a saturated fatty acid. In yet other embodiments of the methods disclosed herein, the GPR40 agonist is selected from the group consisting of GW9508, TAK-875, AMG-837, TUG-469, compound 4p, compound C and pharmaceutically acceptable salts thereof. In some embodiments, the GPR40 agonist is TAK-875 or a pharmaceutically acceptable salt thereof. In those embodiments where the GPR40 agonist comprises TAK-875, an effective amount of the TAK-875 may be about 100 mg/kg/day. In those embodiments where the GPR40 agonist comprises TAK-875, it may be administered to a subject at least once or twice daily. In other embodiments, the GPR40 agonist is GW-9508 or a pharmaceutically acceptable salt thereof.

In some embodiments, exemplary GPR40 agonists for use in the methods disclosed herein include or comprise fatty acids, such as $C_8$-$C_{24}$ fatty acids. In certain embodiments, such fatty acids are unsaturated or polyunsaturated fatty acids. For example, in certain embodiments the GPR40 agonists are or comprise one or more omega-3 polyunsaturated fatty acids selected from the group consisting of eicosapentaenoic acid (EPA), docosahexaenoic acid (DHA) and alpha-linolenic acid (ALA).

Additionally, in other embodiments the contemplated GPR40 agonists comprise one or more compounds or ligands that are capable of modulating the GPR40 (e.g., agonist ligands or compounds that selectively stimulate, activate, bind or otherwise have affinity for GPR40). For example, in certain embodiments, the GPR40 agonist is or comprises TAK-875 and pharmaceutically acceptable salts, esters and pro-drugs thereof. In those embodiments where the GPR40 agonist is or comprises TAK-875, an effective amount of such TAK-875 may be about 100 mg/kg/day (e.g., administered to a human subject affected by melanoma at least one, two, three, four, five, six, or more times daily).

The GPR40 agonist GW9508 may be used in accordance with the methods and compositions disclosed herein. In certain embodiments, the GPR40 agonist is or comprises GW9508 and pharmaceutically acceptable salts, esters and pro-drugs thereof. In other embodiments, the GPR40 agonist is selected from the group of ligands and compounds consisting of GW9508, TAK-875, AMG-837, TUG-469, compound 4p, compound C and pharmaceutically acceptable salts, esters and pro-drugs thereof.

The compositions disclosed herein may be co-administered to a subject (e.g., a human subject with melanoma) in combination with one or more additional therapeutic agents. For example, such compositions may be co-administered to the subject with one or more chemotherapeutic agents. Similarly, such compositions may be co-administered to the subject with one or more antiemetic agents.

Each of the compositions disclosed herein may be administered to a subject through any route of administration. In certain embodiments of the methods disclosed herein, the compositions disclosed herein are formulated for enteral administration to a subject. Alternatively, in the methods disclosed herein, the compositions disclosed herein may be administered to a subject parenterally (e.g., subcutaneously, intramuscularly, transdermally, topically, or intravenously). In certain embodiments, the compositions are prepared for topical administration to a subject.

The above discussed and many other features and attendant advantages of the present invention will become better understood by reference to the following detailed description of the invention when taken in conjunction with the accompanying examples.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1D illustrate the effects of docosahexaenoic acid (DHA) on cell growth. As shown in FIG. 1B, animal weights did not differ between the three different diet groups, however as shown in FIG. 10 and FIG. 1D, tumor weights and volumes were significantly lower in the DHA group as compared to the SOY group.

FIGS. 2A-2D illustrate serum and tumor fatty acid profiles.

FIG. 3A illustrates that the nonselective GPR120 and GPR40 agonist GW9508 has an inhibitory effect on the growth of all three different human melanoma cell lines (A2058, A375, SK-Mel 3) while no toxic effect was observed on the growth of the control fibroblast cell line (Hs27). FIG. 3B shows that GPR40 expression determined by RT-qPCR was higher in the human melanoma cell lines (A2058, A375, SK-Mel 3) compared to the control fibroblast cell line (Hs27) and also compared to the human neuroblastoma and breast cancer cells tested. FIG. 3C illustrates that the selective GPR40 agonist TAK-875 also has a selective inhibitory effect on the growth of all three human melanoma cell lines tested without negatively effecting the growth of the control fibroblast or human breast cancer cell lines even at very high concentrations. FIGS. 3D-G illustrate that TAK-875 administered at 100 mg/kg via once daily orogastric gavage inhibits the growth of established human melanoma tumors in a murine subcutaneous xenograft model of human melanoma. Animal weights were not significantly different between placebo and treatment groups (N=7/group) (FIG. 3D), although tumor weights (FIG. 3E), tumor volumes (FIG. 3F) and change in tumor volume over the 14 day treatment period (FIG. 3G) were lower with TAK-875 treatment compared to placebo.

DETAILED DESCRIPTION OF THE INVENTION

The inventions disclosed herein generally relate to the findings that agonists of the G-coupled protein receptor 40 (GPR40) (e.g., fatty acids) result in an inhibitory (e.g., cytotoxic) effect on certain cancers (e.g., melanoma) and cancer cell lines. In particular, the present inventions demonstrate that GPR40 plays a key role in inhibiting the growth and survival of certain cancer cell types (e.g., neuroblastoma, medullary thyroid carcinoma and malignant peripheral nerve sheath tumors), and agonist stimulation of GPR40, such as by omega-3 fatty acids, activates signaling pathways that inhibit or are useful for the treatment and/or prevention of certain cancers (e.g., melanoma).

Disclosed herein are methods of treating or preventing certain cancers in a subject (e.g., a pediatric subject). Such methods generally comprise a step of administering a composition comprising an effective amount of a GPR40 agonist (e.g., omega-3 fatty acids) to the subject and thereby treating or preventing the cancer. As used herein, the term "cancer" generally refers to any cellular disease, disorder or condition that is characterized by an unregulated or uncontrolled cellular proliferation or a pathologic ability to invade surrounding tissues, organs or structures. In certain embodiments, the cancer is derived from neural crest tissues (e.g., neuroblastoma and melanoma). For example, the cancer may include, but not be limited to, a neuroblastoma, ganglioneuroblastoma, melanoma, carcinoid tumor, pheochromocytoma medullary thyroid carcinoma, malignant peripheral nerve sheath tumors and paraganglioma. In certain embodiments, the cancers that are subject to treatment using the methods and compositions disclosed herein are metastatic or benign cancers. For example, in certain embodiments, the cancer is melanoma. In other embodiments, the cancer is neuroblastoma. In certain embodiments, the cancer is medullary thyroid carcinoma. In other embodiments, the cancer is malignant peripheral nerve sheath tumors. In yet other embodiments, the cancer comprises or is characterized by cancer cells or cell lines that express GPR40. In certain other embodiments, the cancer is not breast cancer or is not derived from breast cancer tissue. In certain other embodiments, the cancer is not a non-neural crest-tissue derived cancer or tumor (e.g., the cancer is a neural crest-derived tumor).

In some embodiments, the composition and methods disclosed herein are useful for inhibiting metastasis of certain cancers (e.g., neuroblastoma, medullary thyroid carcinoma, malignant peripheral nerve sheath tumors and melanoma) in a subject. For example, disclosed herein are methods that generally comprise a step of administering a composition comprising a GPR40 agonist to the subject (e.g., a mammalian subject) to inhibit cancer metastasis.

As discussed in greater detail below, the GPR40 (which is also referred to as free fatty acid receptor 1 or FFA1) represents a novel therapeutic target that can be exploited to mediate inhibitory or cytotoxic effects on cancer cells (e.g., cancer cells expressing GPR40). GPR40 is a cell membrane long-chain fatty acid receptor that is highly expressed in pancreatic islet β-cells, monocytes, and brain and participates in fatty acid augmentation of glucose stimulated insulin secretion. Modulation (e.g., selective agonist stimulation) of the G-protein coupled receptor results in phospholipase C activation, and production of inositol 1,4,5-triphosphate and diacylglycerol, and increased levels of intracellular calcium, which activates caspase-dependent apoptotic pathways (Tsujihata, at al., *J Pharmacol Exp Ther* 339, 228-237 (2011); and Briscoe, et al. *J Bio Chem* 278, 11303-11311 (2003)).

The present inventors have identified GPR40 as the cellular receptor via which the compositions disclosed herein mediate the observed inhibitory effects (e.g., cytotoxicity). Therefore, the compositions and methods disclosed herein relate to the findings that modulation (e.g., selective agonist stimulation) of GPR40 (e.g., by one or more GPR40 agonists) has a strong inhibitory effect on the growth of certain cancer cells, and in particular cancer cells expressing GPR40 (e.g., melanoma, medullary thyroid carcinoma, malignant peripheral nerve sheath tumors and neuroblastoma tumor cells).

In certain embodiments, the methods disclosed herein comprise a step of administering to, or contacting a subject or cancer cells with, one or more GPR40 agonists. As used therein, the phrases "G-coupled protein 40 agonist" or "GPR40 agonists" broadly refer to any compounds, agents or ligands capable of modulating GPR40 (e.g., by selective agonist activation or stimulation of GPR40). GPR40 agonists may be endogenous or exogenous agonists of GPR40. In certain embodiments, such modulation of GPR40 by a GPR40 agonist mediates or otherwise induces an inhibitory or cytotoxic effect on the targeted cells (e.g., certain cancer cells expressing GPR40). For example, targeted melanoma cells may be contacted with one or more GPR40 agonists such as a poly unsaturated fatty acid (e.g., an omega-3 fatty acid such as docosahexaenoic acid), which in turn will induce or mediate an inhibitory effect on such targeted melanoma cells.

In certain embodiments, the GPR40 agonist is selected from one of the number of known or available GPR40 agonist compounds, for example one or more of the GPR40 agonists disclosed in Blad, et al., *Nature Rev. Drug. Discov.* 11, 603-619 (2012), the entire contents of which are incorporated herein by reference. In certain embodiments, the GPR40 agonist is or comprises TAK-875 and pharmaceutically acceptable salts, esters and pro-drugs thereof (Burant, at al., *Lancet* 379, 1403-1411 (2012); and Tsujihata, at al., *J. Pharmacol. Exp. Ther.* 339, 228-237 (2011)). In certain embodiments, TAK-875 and other selective GPR40 agonist may provide enhanced efficacy or may demonstrate a stronger or more potent inhibitory effect relative to, for example, omega-3 fatty acids such as DHA. In some embodiments, the GPR40 agonist is a thiazolidinedione compound (e.g., pioglitazone, rosiglitazone or troglitazone). In some embodiments, the GPR40 agonist is or comprises TUG-469 and pharmaceutically acceptable salts, esters and pro-drugs thereof (Christiansen, at al., *J. Med. Chem.* 54, 6691-6703 (2011); and Walsh, at al., *Bioorg. Med. Chem. Lett.* 21, 3390-3394 (2011)). In yet other embodiments, the GPR40 agonist is or comprises AMG-837 and pharmaceutically acceptable salts, esters and pro-drugs thereof (Lin, et al., *PLoS ONE* 6, e27270 (2011); and Houze, et al., *Bioorg. Med. Chem. Lett.* 22, 1267-1270 (2012)). In other embodiments, the GPR40 agonist is or comprises GW9508 and pharmaceutically acceptable salts, esters and pro-drugs thereof (Briscoe, et al., *Br. J. Pharmacol.* 148, 619-628 (2006)). In some embodiments, the GPR40 agonist is or comprises Compound 4p and pharmaceutically acceptable salts, esters and pro-drugs thereof (Mikami, et al., *J. Med. Chem.* 55, 3756-3776 (2012)). In certain embodiments, the GPR40 agonist is or comprises Compound 7, AM-1638 or AM-6226 and pharmaceutically acceptable salts, esters and pro-drugs thereof (Walsh, et al., *Bioorg. Med. Chem. Lett.* 21, 3390-3394 (2011)). In certain embodiments, the GPR40 agonist is or comprises Compound 22 and pharmaceutically acceptable salts, esters and pro-drugs thereof (Song, et al. *J. Med. Chem.* 50, 2807-2817 (2007)). In yet other embodiments, the GPR40 agonist is or comprises Compound C and pharmaceutically acceptable salts, esters and pro-drugs thereof (Zhou, et al., *Bioorg. Med. Chem. Lett.* 20, 1298-1301 (2010)).

In certain embodiments, the GPR40 agonist is a fatty acid. Such fatty acids may be saturated, monounsaturated or polyunsaturated. In some embodiments, the GPR40 agonist is or comprises one or more polyunsaturated fatty acids, such as omega-3 or omega-6 fatty acids. Omega-3 fatty acids are fatty acids with an unsaturated double bond in the third carbon position from the methyl terminal of the fatty acid. Omega-6 fatty acids are fatty acids with an unsaturated double bond in the sixth carbon position from the methyl terminal of the fatty acid. In certain embodiments, the GPR40 agonist may be or comprise one or more of the polyunsaturated omega-3 fatty acids alpha-linolenic acid (ALA), docosahexaenoic acid (DHA), and eicosapentaenoic acid (EPA). In yet other embodiments, the fatty acids are selected from the group consisting of alpha-linolenic acid (ALA), docosapentaenoic acid (DPA), docosahexaenoic acid (DHA), eicosatrienoic acid (ETE), eicosatetraenoic acid (ETA), eicosapentaenoic acid (EPA), heneicosapentaenoic acid (HPA), hexadecatrienoic acid (ETA), stearidonic acid (SEA), Tetracosapentaenoic acid and Tetracosahexaenoic acid. In certain embodiments, the GPR40 agonist may be or comprise one or more of the polyunsaturated omega-6 fatty acids selected from the group consisting of linoleic acid, gamma-linolenic acid, calendic acid, eicosadienoic acid, dihomo-gamma-linolenic acid, arachidonic acid, docosadienoic acid, adrenic acid, docosapentaenoic acid, tetracosatetraenoic acid and tetracosapentaenoic acid.

In certain embodiments, the GPR40 agonist is or comprises a $C_8$-$C_{24}$ fatty acid. For example, such a $C_8$-$C_{24}$ fatty acid agonist may be an unsaturated or polyunsaturated $C_8$-$C_{24}$ fatty acid. In other embodiments, such a $C_8$-$C_{24}$ fatty acid may be a saturated $C_8$-$C_{24}$ fatty acid.

In contrast to the 1:1 ratio of omega-6 to omega 3 fatty acids ratio historically consumed by humans, the current Western diet is composed of an omega-6 to omega-3 fatty acid ratio between 10:1 and 25:1. In certain embodiments, the present inventions relate to compositions and methods that facilitate or promote the correction of observed shifts in the relative and absolute consumption of omega-6 and omega-3 fatty acids that have occurred in Western societies since the time of the Industrial Revolution. For example, contemplated herein are methods of reducing or mitigating a subject's risk for developing certain cancers (e.g., melanoma) by modulating the subject's diet such that the ratio of omega-6 to omega-3 fatty acids approaches about 1:1. In certain embodiments, an effective amount of the fatty acid GPR40 agonist (e.g., the omega-3 fatty acid DHA) shifts the 10:1 to 25:1 ratio of omega-6 to omega-3 fatty acids of the current Western diet towards a 1:1 ratio of omega-6 to omega 3 fatty acids ratio. For example, an effective amount of omega-3 fatty acids may be calculated based on the amount of dietary omega-6 fatty acids consumed by a subject, such that the ratio of omega-6 to omega-3 fatty acids is about 1:1. In some embodiments, the methods disclosed herein contemplate contacting cancer cells with about 10-300 µM of an omega-3 fatty acid, such as DHA. In some embodiments, an effective amount of an omega-3 fatty acid GPR40 agonist is not achievable through dietary intake or dietary supplementation. For example, the amount of an omega-3 fatty acid (e.g., DHA) necessary to modulate GPR40 may well exceed those amounts achieved with diet alone or may otherwise exceed recommended daily intake amount of the omega-3 fatty acid.

In certain aspects, the methods of the present invention comprise the administration of an effective amount of one or more GPR40 agonists (e.g., TAK-875 and pharmaceutically acceptable salts thereof) to a subject having or at risk for developing certain cancers (e.g., melanoma). In some embodiments, the methods disclosed herein contemplate contacting cancer cells with about 0.1-10 µM of TAK-875. As used herein, the term "subject" means any mammal, including humans. In certain embodiments of the present invention the subject is an adult or an adolescent. In some embodiments the subject is a pediatric subject. In certain other embodiment, the subject does not have diabetes mellitus. In yet other embodiments, the subject does not have breast cancer. In other embodiments, the subject does not have a non-neural crest tissue-derived cancer or tumor.

Cellular variability in GPR40 expression may provide critical information regarding the efficacy of the methods disclosed herein. Accordingly, in some embodiments, the methods described herein may further comprise one or more steps of screening a cancer cell or a cancer cell line to determine the degree to which such cell or cell line expresses GPR40. Such screening may be performed prior to administering one or more of the compositions disclosed herein to a subject. For example, prior to performing one or more of the methods disclosed herein, a subject's tumor (e.g., melanoma tumor) may be biopsied and subjected to immunohistochemistry analysis (e.g., using one or more optimized GPR40 antibody, flow cytometry and RT-pPCR quantification or other routine means known to one of skill in the art) to determine whether and to what degree such tumor cells express GPR40. If such tumor cells express GPR40 or express GPR40 to a high degree, such tumor may be a candidate for treatment in accordance with the teachings disclosed herein. Similarly, if such tumor cells do not express GPR40, such tumor may be a poor candidate for treatment in accordance with the teachings disclosed herein or alternatively.

In certain embodiments, the inventions disclosed herein relate to methods of contacting certain cancer cells or cell lines (e.g., a human melanoma cell line) using the compositions disclosed herein (e.g., compositions comprising one or more omega-3 fatty acids). As the term is used herein, "contacting" generally refers to bringing two or more compositions or molecules (e.g., a cancer cell and a composition disclosed herein) into close proximity with each other such that the compositions or molecules can react or otherwise interact with each other. A step of contacting may be performed in vitro, ex vivo or in vivo. For example, in certain embodiments a human melanoma cell may be contacted with one or more omega-3 fatty acids (e.g., EPA, DHA and/or ALA).

As used herein, the phrase "effective amount" means an amount sufficient to achieve a meaningful benefit (e.g., treating or otherwise preventing certain cancers), preferably with an acceptable risk of adverse effects. An effective amount of a GPR40 agonist (e.g., TAK-875) in the compositions of the present invention may be generally determined based on the ability of such GPR40 agonist to suppress or otherwise inhibit cancer cell growth and survival. Generally, the amount of a composition or GPR40 agonist administered to a subject will depend upon the characteristics of the subject and the severity of the subject's cancer. In certain embodiments, the compositions may be administered to a subject (e.g., administered orally) once daily, twice daily, three times daily, four times daily, five times daily, six times daily, seven times daily, eight times daily, or more.

The compositions of the present invention can be administered to a subject by any suitable routes of administration. Preferably, following the administration of such compositions a therapeutic concentration of the GPR40 agonist (e.g., omega-3 fatty acids) is achieved and/or maintained in the affected cells, organs or tissues (e.g., plasma) of the subject. In certain embodiments, the composition is combined with suitable excipients and formulated for topical or transdermal administration. Alternatively, in certain embodiments, the compositions of the present invention may be prepared for enteral or parenteral administration. General techniques applicable to the formulation and administration of the compositions of the present invention may be found in "Remington's Pharmaceutical Sciences," Mack Publishing Co., Easton, Pa., latest edition.

The compositions of the present invention can also be administered or co-administered as part of a therapeutic regimen with other suitable therapeutic or prophylactic agents (e.g., administered concurrently or sequentially). For example, the compositions disclosed herein may be formulated or co-administered with one or more additional therapeutic agents (e.g., one or more chemotherapeutics or anti-emetics).

The articles "a" and "an" as used herein in the specification and in the claims, unless clearly indicated to the contrary, should be understood to include the plural referents. claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The entire contents of all of the references (including literature references, issued patents and published patent applications and websites) cited throughout this application are hereby expressly incorporated by reference.

The embodiments described herein will be further illustrated by the following Examples, which should not be construed as limiting.

EXAMPLES

Example 1

To understand the relationship between dietary fatty acids and human melanoma the present studies were performed. Specifically, the cytotoxic effects of the omega-3 fatty acid docosahexaenoic acid (DHA) on each of the A2058, A375 and SK-Mel3 human melanoma cell lines were evaluated relative to the effects that DHA had on a human foreskin fibroblast (Hs27) control cell line.

The human foreskin fibroblast (Hs27) and human melanoma (A2058, A375, SK-Mel 3) cell lines were purchased from ATCC (Manassas Va.). Cells were plated in 48-well plates at a concentration of $7.5 \times 10^3$ cells/well in either DMEM (Hs27, A2058, A375; Invitrogen/GIBCO, Grand Island N.Y.) or McCoy's 5a medium (SK-Mel 3; Invitrogen/GIBCO) supplemented with 10% FBS (Invitrogen/GIBCO) and incubated at 37° C. in a humidified atmosphere with 5% $CO_2$. After 24 hours the medium was replaced with either DMEM (HS27, A2058, A375) or McCoy's 5a Medium (SK-Mel 3) containing 1% heat inactivated-PBS (Invitrogen/GIBCO) and 0.1% FA-free BSA (Invitrogen/GIBCO) with various concentrations of DHA (Martek, Columbia Md.) prepared in 4 µL of ETOH. DHA was provided at 25-250 µM, and in the studies that follow GW9508 was provided at 25-150 µM and TAK-875 was provided at 0-0.4 µM. Controls were treated with 4 µL of ETOH. All concentrations were tested in quadruplicate.

Following 144 hours of DHA treatment cells were trypsinized (Trypsin-EDTA; Invitrogen/GIBCO) and viable cells were counted using an absorbance-based cell viability assay (Cell Titer Blue Cell Viability Assay; Promega, Madison Wis.). During the treatment, medium was changed at 72 hours for the DHA studies. Cell counts were reported as a percent of the control cell count.

Figures 1A, 1B, 1C, 1D:
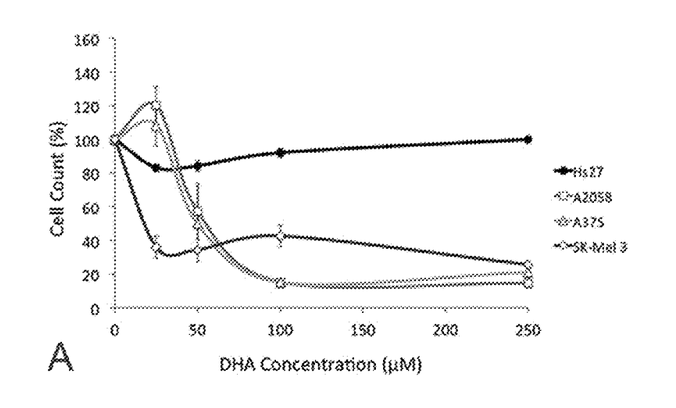
FIG. 1A Illustrates the effects of DHA on the growth of three different human melanoma cell lines (A2058, A375 and SK-Me13) relative to a control fibroblast cell line (Hs27).
FIGS. 1B-D illustrate the effects observed in a murine subcutaneous xenograft model of human melanoma (A2058) that was used to evaluate and compare the effect of a diet rich in DHA on the growth of human melanoma, relative to an omega-6 fatty acid-rich diet (SOY) and a control diet which was deficient in essential fatty acids (EFAD) (n=19/group).

As illustrated in FIG. 1A, DHA had a profound and selective cytotoxic effect on each of the A2058, A375 and SK-Mel3 human melanoma cell lines. As also depicted in FIG. 1A, DHA displayed no growth inhibition on the control fibroblast Hs27 cell line. The foregoing findings therefore support the conclusion that omega-3 fatty acids such as DHA strongly inhibit the growth of human melanoma in vitro and have a profound inhibitory effect on human melanoma cell lines.

Example 2

To further evaluate the effects that dietary treatment with omega-3 fatty acids have on melanoma in vivo, a subcutaneous murine xenograft model of human melanoma was used.

The subcutaneous murine xenograft model of human melanoma was created in 6-week old severe combined immunodeficiency (SCID) mice (Jackson Laboratories, Bar Harbor, Me.) by subcutaneous injection of $1 \times 10^6$ human melanoma cells (A2058) in 0.2 µL of PBS (Invitrogen/GIBCC) into the left flank of each animal. Animal weights and tumor dimensions were measured every 48 hours. Tumor volume was calculated using the following formula: volume=length×width$^2$×0.52.

An omega-3 fatty acid rich diet was designed to mimic the fatty acid composition of cold water fish, with an omega-3 to omega-6 fatty acid ratio of 20:1 provided as DHA and arachidonic acid (AA; 20:4n-6; omega-6 fatty acid). In contrast an omega-6 fatty acid rich diet was designed to mimic the standard Western diet, with fat provided as soybean oil and thus containing an omega-6 to omega-3 fatty acid ratio of approximately 8:1, provided as linoleic acid (LA; 18:2n-6; omega-6 fatty acid) and alpha-linolenic acid (ALA; 18:3n-3; omega-3 fatty acid). A third diet, in which all fat was provided as hydrogenated coconut oil, which is deficient in essential fatty acids, was used as a control for essential fatty acid deficiency (EFAD).

Animals were randomized to one of three different diet groups (N=19/group), each containing 10% of total calories as fat provided as: soybean oil (SOY; #110990, Dyets Inc., Bethlehem Pa., USA), hydrogenated coconut oil (HCO; #102328, Dyets Inc.) or a 20:1 ratio of DHA:AA (DHA; #102536, Dyets Inc.) (Table 1). Animals in the dietary treatment arm of the study were pre-treated with their respective diet for three weeks prior to tumor cell inoculation and continued throughout the study period.

TABLE 1

Composition of Experimental Diets

| | HCO | SOY | DHA |
|---|---|---|---|
| Casein | 501.2 | 501.2 | 501.2 |
| L-Cystine | 7.2 | 7.2 | 7.2 |
| Sucrose | 400 | 400 | 400 |
| Cornstarch | 1676.5 | 1676.5 | 1676.3 |
| Dyetrose | 589 | 589 | 589 |
| Mineral Mix #210050 | 29.4 | 29.4 | 29.4 |
| Vitamin Mix #310025 | 38.7 | 38.7 | 38.7 |
| Hydrogenated Coconut Oil | 360 | 0 | 284.4 |
| Soybean Oil | 0 | 360 | 0 |
| Docosahexaenoic Acid (DHA) | 0 | 0 | 72 |
| Arachidonic Acid (AA) | 0 | 0 | 3.6 |
| Total | 3602.0 | 3602.0 | 3601.8 |

All values reported as kcal/kg diet.

Although animals in each of the dietary treatment groups (N=19/group) had similar body weights (FIG. 1B), tumors were 69% smaller in weight (P=0.005; FIG. 10) and 76% smaller in volume (P=0.001; FIG. 1D) in the DHA compared to the SOY group. Animals in the EFAD group had tumors comparable to the SOY group.

Figure 2A:
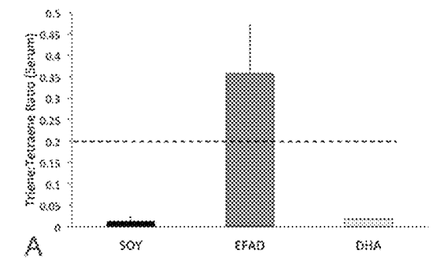
FIGS. 2A-D illustrate serum fatty acid profiles following dietary treatment and demonstrate biochemical essential fatty acid deficiency (EFAD), defined as a triene:tetraene ratio>0.2, in the EFAD group only (FIG. 2A), while serum omega-6 fatty acid content was significantly lower and omega-3 fatty acid content was significantly higher in the DHA group compared to the SOY group (FIGS. 2B-D).

No animals in either the SOY or the DHA diet groups had any evidence of biochemical essential fatty acid deficiency (serum triene:tetraene ratio>0.2). In contrast, as shown in FIG. 2A and in Table 2 below, all animals on the EFAD diet had evidence of biochemical EFAD.

TABLE 2

Serum fatty acid profiles

| Fatty acid | SOY (N = 5) | EFAD (N = 5) | DHA (N = 5) | $P_{ANOVA}$ | $P_{SOY\ vs\ DHA}$ |
|---|---|---|---|---|---|
| Saturated Fats | | | | | |
| Tetradecanoic (myristic) acid, 14:0 | 0.769 ± 0.332 | 3.042 ± 0.816 | 2.197 ± 0.841 | 0.006 | 0.017 |
| Hexadecanoic (palmitic) acid, 16:0 | 19.576 ± 1.674 | 19.341 ± 0.632 | 20.585 ± 0.715 | 0.145 | 0.270 |
| Octadecanoic (stearic) acid, 18:0 | 12.289 ± 2.611 | 12.049 ± 1.107 | 10.890 ± 0.382 | 0.395 | 0.691 |
| Monounsaturated Fats | | | | | |
| Hexadecenoic (palmitoleic) acid, 16:1ω7 | 3.122 ± 0.918 | 5.495 ± 1.003 | 4.245 ± 0.627 | 0.006 | 0.058 |
| Octadecenoic (vaccenic) acid, 18:1ω7 | 1.891 ± 0.733 | 3.158 ± 0.520 | 1.795 ± 0.386 | 0.019 | 0.805 |
| Octadecenoic (oleic) acid, 18:1ω9 | 14.041 ± 1.968 | 18.521 ± 0.811 | 13.825 ± 0.997 | 0.009 | 0.835 |
| Polyunsaturated Fats | | | | | |
| Octadecatrienoic (alpha-linolenic) acid, 18:3ω3 | 1.366 ± 0.584 | 0.098 ± 0.042 | 0.081 ± 0.031 | 0.009 | 0.008 |
| Eicosapentaenoic (trimnodonic) acid, 20:5ω3 | 0.553 ± 0.104 | 0.161 ± 0.046 | 5.049 ± 1.545 | 0.002 | 0.008 |
| Docosapentaenoic (clupanodonic) acid, 22:5ω3 | 0.489 ± 0.159 | 0.093 ± 0.028 | 1.044 ± 0.150 | 0.002 | 0.001 |
| Docosahexaenoic acid, 22:6ω3 | 5.911 ± 0.730 | 3.430 ± 0.339 | 19.284 ± 3.101 | 0.002 | 0.008 |
| Octadecadienoic (linoleic) acid, 18.2ω6 | 20.754 ± 2.426 | 10.432 ± 0.755 | 8.028 ± 1.569 | 0.003 | <0.001 |
| Octadecatrienoic (gamma-linolenic) acid, 18:3ω6 | 0.309 ± 0.130 | 0.181 ± 0.044 | 0.041 ± 0.017 | 0.005 | 0.008 |
| Eicosatrienoic (dihomo-gamma-linolenic) acid, 20:3ω6 | 1.540 ± 0.259 | 1.613 ± 0.266 | 0.460 ± 0.159 | 0.009 | <0.001 |
| Eicosatetraenoic (arachidonic) acid, 20:4ω6 | 14.313 ± 2.248 | 10.902 ± 2.288 | 7.477 ± 0.436 | 0.005 | 0.008 |
| Eicosatrienoic (mead) acid, 20:3ω9 | 1.164 ± 0.066 | 3.732 ± 0.919 | 1.129 ± 0.037 | 0.008 | 0.354 |
| Totals | | | | | |
| Total ω3 | 8.318 ± 1.214 | 3.782 ± 0.314 | 25.459 ± 4.486 | 0.002 | 0.008 |
| Total ω6 | 37.742 ± 4.109 | 23.727 ± 2.909 | 16.133 ± 1.778 | 0.002 | <0.001 |
| Total ω9 | 14.916 ± 2.028 | 23.274 ± 0.938 | 14.534 ± 1.103 | 0.009 | 0.724 |
| Total ω-7 | 2.234 ± 0.819 | 3.333 ± 0.531 | 1.884 ± 0.417 | 0.032 | 0.433 |
| Total saturated FA | 33.385 ± 1.780 | 38.715 ± 2.519 | 37.722 ± 2.306 | 0.012 | 0.013 |
| Total monounsaturated FA | 20.108 ± 3.260 | 28.371 ± 1.502 | 20.541 ± 1.808 | 0.009 | 0.804 |
| Total polyunsaturated FA | 46.507 ± 3.860 | 32.915 ± 3.186 | 41.736 ± 3.373 | 0.005 | 0.076 |
| Ratios | | | | | |
| Triene:Tetraene ratio | 0.012 ± 0.006 | 0.357 ± 0.130 | 0.017 ± 0.004 | 0.005 | 0.135 |
| ω6/ω3 ratio | 4.636 ± 0.999 | 6.289 ± 0.711 | 0.653 ± 0.151 | 0.003 | 0.008 |

All values represent percent ± SD.

Figure 2B:
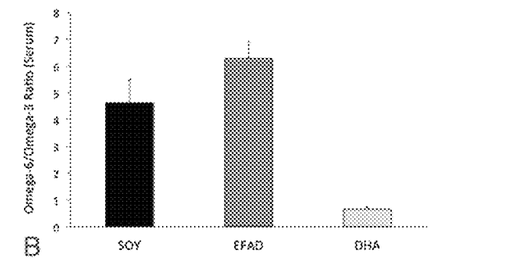
Figure 2C:
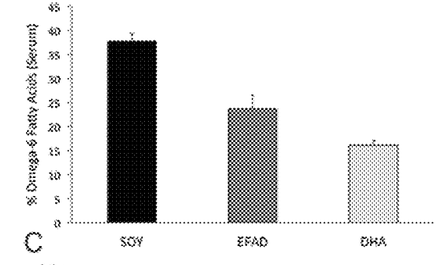
Figure 2D:
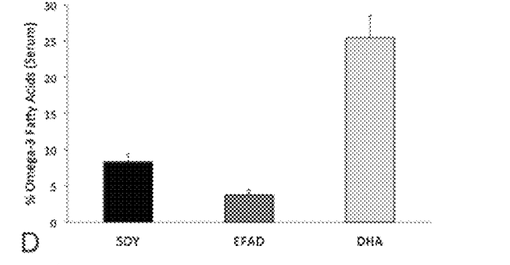
Figure 2E:
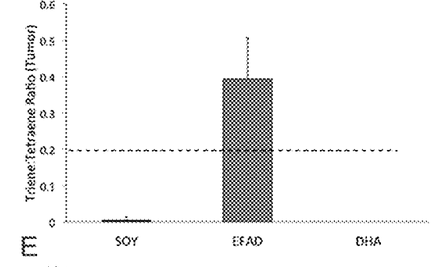
As shown in FIGS. 2E-H, tumor fatty acids profiles following dietary treatment also demonstrated EFAD only in tumors from animals on the EFAD diet (FIG. 2E). The tumors from animals on the DHA diet had omega-6 and omega-3 fatty acid contents very similar to those seen in the serum (FIGS. 2F-H).
Figure 2F:
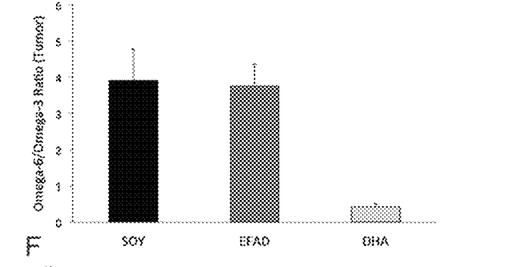
Figure 2G:
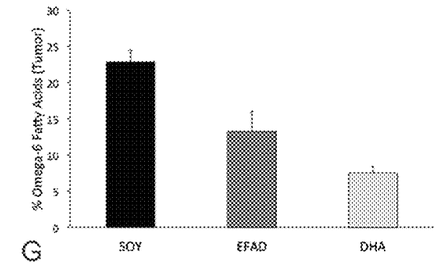
Figure 2H:
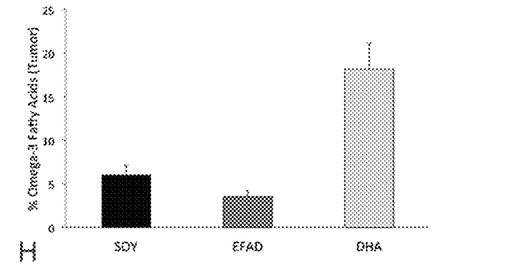

The dietary treatments did significantly change the serum FA profiles resulting in a lower omega-6/omega-3 fatty acid ratio in the DHA compared to the SOY and DEAD groups (FIGS. 2B-D). Interestingly, the serum omega-6/omega-3 ratio in the SOY group (4.64±1.00) was very similar to the ratio reported for humans consuming a typical Western diet (4.72±0.19). As shown in FIGS. 2E-H and in Table 3 below, the tumor fatty acid profiles reflected the serum fatty acid profiles.

TABLE 3

Tumor fatty acid profiles

| Fatty acid | SOY (N = 4) | EFAD (N = 5) | DHA (N = 5) | $P_{ANOVA}$ | $P_{SOY\ vs\ DHA}$ |
|---|---|---|---|---|---|
| Saturated Fats | | | | | |
| Tetradecanoic (myristic) acid, 14:0 | 2.391 ± 0.729 | 3.557 ± 0.582 | 2.858 ± 0.470 | 0.040 | 0.330 |
| Hexadecanoic (palmitic) acid, 16:0 | 22.064 ± 3.647 | 22.428 ± 0.855 | 23.862 ± 1.500 | 0.243 | 0.423 |
| Octadecanoic (stearic) acid, 18:0 | 13.860 ± 1.522 | 12.979 ± 0.780 | 13.772 ± 0.818 | 0.325 | 0.922 |
| Monounsaturated Fats | | | | | |
| Hexadecenoic (palmitoleic) acid, 16:1ω7 | 4.820 ± 2.189 | 8.663 ± 1.508 | 6.853 ± 1.209 | 0.050 | 0.171 |
| Octadecenoic (vaccenic) acid, 18:1ω7 | 4.298 ± 1.559 | 6.654 ± 0.776 | 5.233 ± 0.585 | 0.018 | 0.338 |
| Octadecenoic (oleic) acid, 18:1ω9 | 20.888 ± 2.708 | 22.425 ± 2.600 | 19.470 ± 2.497 | 0.221 | 0.450 |
| Polyunsaturated Fats | | | | | |
| Octadecatrienoic (alpha-linolenic) acid, 18:3ω3 | 0.468 ± 0.376 | 0 | 0 | 0.002 | NA |
| Eicosapentaenoic (trimnodonic) acid, 20:5ω3 | 0.009 ± 0.0123 | 0 | 1.305 ± 0.316 | 0.004 | 0.020 |
| Docosapentaenoic (clupanodonic) acid, 22:5ω3 | 0.529 ± 0.071 | 0.094 ± 0.086 | 2.172 ± 0.415 | 0.003 | 0.016 |
| Docosahexaenoic acid, 22:6ω3 | 4.894 ± 1.037 | 3.455 ± 0.666 | 14.646 ± 2.350 | 0.003 | <0.001 |
| Octadecadienoic (linoleic) acid, 18.2ω6 | 13.850 ± 3.206 | 5.289 ± 0.750 | 4.177 ± 0.693 | 0.008 | 0.0016 |
| Octadecatrienoic (gamma-linolenic) acid, 18:3ω6 | 0 | 0 | 0 | NA | NA |

TABLE 3-continued

Tumor fatty acid profiles

| Fatty acid | SOY (N = 4) | EFAD (N = 5) | DHA (N = 5) | $P_{ANOVA}$ | $P_{SOY\ vs\ DHA}$ |
|---|---|---|---|---|---|
| Eicosatrienoic (dihomo-gamma-linolenic) acid, 20:3ω6 | 0.351 ± 0.237 | 1.583 ± 2.276 | 0.126 ± 0.082 | 0.022 | 0.166 |
| Eicosatetraenoic (arachidonic) acid, 20:4ω6 | 5.289 ± 0.995 | 4.763 ± 0.543 | 2.718 ± 0.490 | 0.010 | 0.009 |
| Eicosatrienoic (mead) acid, 20:3ω9 | 0.020 ± 0.039 | 1.880 ± 0.602 | 0 | 0.004 | NA |
| Totals | | | | | |
| Total ω3 | 6.008 ± 1.105 | 3.548 ± 0.688 | 18.124 ± 3.050 | 0.003 | <0.001 |
| Total ω6 | 22.836 ± 1.626 | 13.215 ± 2.776 | 7.511 ± 0.915 | 0.003 | <0.001 |
| Total ω9 | 22.378 ± 2.939 | 26.250 ± 2.195 | 20.603 ± 2.553 | 0.026 | 0.377 |
| Total ω-7 | 4.554 ± 1.557 | 7.325 ± 0.974 | 5.557 ± 0.613 | 0.020 | 0.311 |
| Total saturated FA | 38.984 ± 4.270 | 40.175 ± 1.854 | 41.325 ± 2.007 | 0.566 | 0.369 |
| Total monounsaturated FA | 31.732 ± 2.860 | 40.349 ± 2.960 | 33.040 ± 3.794 | 0.015 | 0.577 |
| Total polyunsaturated FA | 29.283 ± 1.486 | 19.466 ± 3.787 | 25.634 ± 3.290 | 0.014 | 0.078 |
| Ratios | | | | | |
| Triene:Tetraene ratio | 0.005 ± 0.010 | 0.394 ± 0.113 | 0 | 0.004 | NA |
| ω6/ω3 ratio | 3.916 ± 0.863 | 3.756 ± 0.606 | 0.422 ± 0.080 | 0.011 | 0.016 |

All values represent percent ± SD.

The foregoing findings therefore support the conclusion that omega-3 fatty acids such as DHA strongly inhibit the growth of human melanoma in vitro and in vivo and have a profound inhibitory effect on human melanoma cell lines. Additionally, such findings support the conclusion that correction of the observed shifts in the relative and absolute consumption of omega-6 and omega-3 fatty acids that have occurred in Western societies may reduce or mitigate a subject's risk for developing certain cancers (e.g., melanoma).

Example 3

The mechanisms via which omega-3 fatty acids exert their cellular effects are largely unknown, however recent studies suggest that in certain cell types these cellular effects of omega-3 fatty acids are mediated via the G-protein coupled receptors 120 and 40 (GPR120 and GPR40) (Oh, et al., Cell 142, 687-698 (2010)). To further understand the mechanism by which omega-3 fatty acids demonstrate an inhibitory effect on melanoma cell lines the following studies were performed. In particular, the instant studies were performed by assessing the affects that GW9508 (an agonist of both GPR120 and GPR40) had on the growth of the A2058, A375 and SK-Mel3 human melanoma cell lines in vitro relative to a control fibroblast cell line (Hs27).

Human foreskin fibroblast (Hs27) and human melanoma (A2058, A375, SK-Mel 3) cell lines (ATCC, Manassas Va.) were plated in 48-well plates at a concentration of 7.5× $10^3$ cells/well in either DMEM (Hs27, A2058, A375; Invitrogen/GIBCC, Grand Island N.Y.) or McCoy's 5a Medium (SK-Mel 3; Invitrogen/GIBCO) supplemented with 10% FBS (Invitrogen/GIBCO) and incubated at 37° C. in a humidified atmosphere with 5% $CO_2$. After 24 hours the medium was replaced with either DMEM (HS27, A2058, A375) or McCoy's 5a Medium (SK-Mel 3) containing 1% heat inactivated-FBS (Invitrogen/GIBCO) and 0.1% FA-free BSA (Invitrogen/GIBCO) with various concentrations of GW9508 (Cayman Chemical, Ann Arbor Mich.) prepared in 4 μL of ETOH, as described in Example 1. Controls were treated with 4 μL of ETOH. All concentrations were tested in quadruplicate.

Following 72 hours of treatment (GW9508) cells were trypsinized (Trypsin-EDTA; Invitrogen/GIBCO) and viable cells were counted using an absorbance-based cell viability assay (Cell Titer Blue Cell Viability Assay; Promega, Madison Wis.). Cell counts are reported as a percent of the control cell count.

Figure 3A:
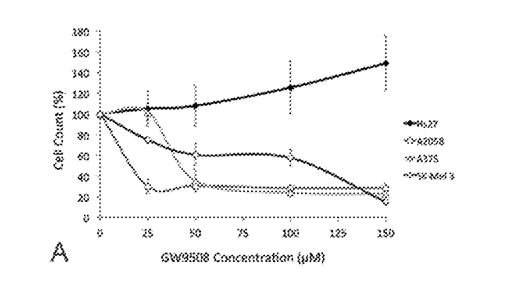
FIG. 3A-3G depict the effect of SPR agonists on the growth of human melanoma.

As illustrated in FIG. 3A, GW9508 had a profound inhibitory effect on the growth of the three different human melanoma cell lines (A2058, A375 and SK-Mel3) relative to a control fibroblast cell line (Hs27). Furthermore, as also illustrated in FIG. 3A, GW9508 was not toxic in the control fibroblast cultures.

In an effort to determine whether the observed inhibitory effects of GW9508 on the human melanoma cell lines were mediated via GPR40, real-time quantitative polymerase chain reaction (RT-qPCR) analyses were performed. To perform such analyses, total RNA was extracted from purified human fibroblast cell lines (Hs27), human melanoma cell lines (A2058, A237, SK-Mel3), human neuroblastoma cell lines (SKNSH, IMR32, SKNAS; ATCC) and human breast cancer cell lines (MCF7; ATCC), suspended in PBS (Invitrogen/GIBCO) using a commercially available kit (Allprep DNA/RNA/Protein Mini Kit; QIAGEN, Valencia Calif.). RNA concentration and quality was analyzed in a Nanodrop ND-1000 spectrophotometer (Nanodrop Technologies, Wilmington Del.). RT-qPCR was performed on an Applied Biosystems 7000 Real-Time PCR System using RNA at 10 ng/mL, a Taqman probe for human GPR40 (Hs03045166_s1; Applied Biosystems, Grand Island N.Y.), human GPR120 (Hs00699184_m1; Applied Biosystems) and human GAPDH (Hs02758991_g1; Applied Biosystems) as an endogenous control and Taqman reagents under default conditions. All assays were performed in duplicate.

Figure 3B:
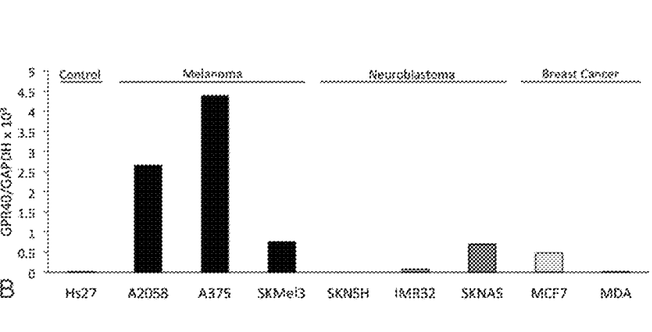

RT-qPCR analyses revealed that the expression of GPR120 by the human melanoma and the control fibroblast cell lines was negligible. In contrast, as illustrated in FIG. 3B, the expression of GPR40 was significantly higher in all three human melanoma cell lines while being negligible in the control fibroblast cell line. The expression of GPR40 in other malignancies was also evaluated and was found to be overall lower in both neuroblastoma and breast cancer cells, as compared to human melanoma. The foregoing findings support the conclusion that the observed inhibitory effect on the human melanoma cell lines was mediated via the GPR40.

Example 4

Given the high expression of GPR40 and the negligible expression of GPR120 by the human melanoma cells evaluated, further studies were performed using the selective, potent and orally bioavailable GPR40 agonist, TAK-875 (Selleck Chemicals) consistent with the methods disclosed in Examples 1 and 3. In particular, such studies were performed to evaluate the ability of TAK-875 to exert an inhibitory effect on human melanoma cell lines in vitro relative to a control fibroblast cell line (Hs27) and the human breast cancer cell line MCF-7, as well as to further evaluate the mechanisms via which compounds such as omega-3 fatty acids exert their cellular effects on human melanoma.

Figure 3C:
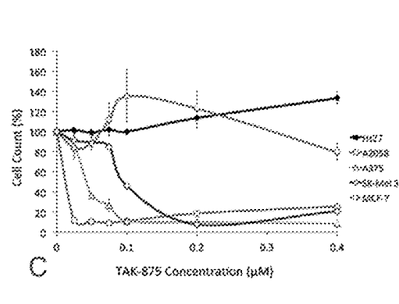

As illustrated in FIG. 3C, TAK-875 demonstrated a robust and selective cytotoxic effect on all of the melanoma cells evaluated (A2058, A375 and SK-Mel3), but did not influence the growth of control fibroblasts nor of the human breast cancer cell line MCF-7. Since each of the cell lines evaluated express GPR40, the foregoing suggests that the toxic effects mediated by TAK-875 via GPR40 may be limited to the melanoma cell lines.

Figure 3D:
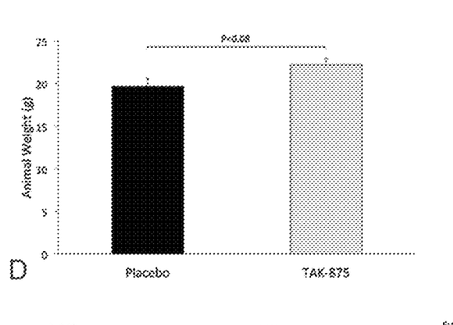
Figure 3E:
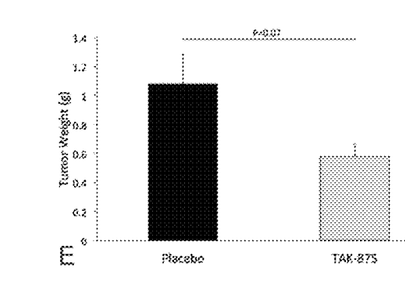
Figure 3F:
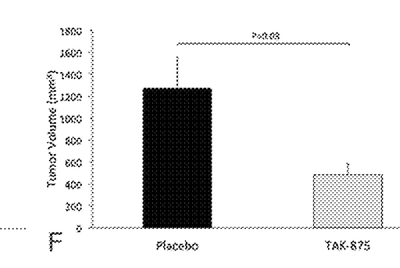
Figure 3G:
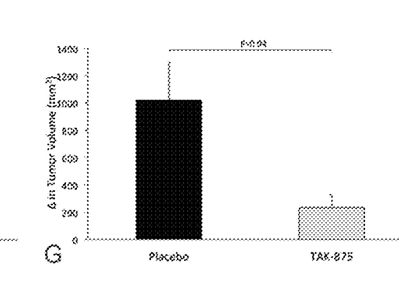

In accordance with the methods disclosed in Example 2, a murine subcutaneous xenograft model of human melanoma was prepared and used to test the effect of once daily oral TAK-875 on the growth of established melanoma tumors in vivo. Animals were treated daily for 14 days with either a control solution or an oral solution of TAK-875 (100 mg/kg/day) from the time their tumor volume reached 200 mm$^3$. Animal weights were not significantly different between the placebo and TAK-875 groups (N=7/group; FIG. 3D), however, tumors were 46% smaller in weight (P=0.07, FIG. 3E) and 62% smaller in volume (P=0.03, FIG. 3F) in the TAK-875 group. Most importantly the change in tumor volume from start of drug treatment to completion of 14 days of treatment, was 77% lower in the TAK-875 group compared to placebo (P=0.04, FIG. 3G).

The foregoing studies confirm that GPR40 plays a key role in mediating the inhibitory effects of dietary omega-3 fatty acids on human melanoma cell growth and survival and confirm that the GPR40 represents an attractive target for the treatment of certain cancers. The foregoing studies further demonstrate that selective agonist stimulation of GPR40 (e.g., with the GPR40 agonist TAK-875) has a strong inhibitory effect on melanoma growth and cell death in culture, as well as in a murine model of human melanoma.

Example 5

Melanoma is a neural crest derived-tumor and, in advanced stages, melanoma and other neural crest-derived tumors, such as medullary thyroid, malignant peripheral nerve sheath tumor (MPNST) and neuroblastoma, have limited available treatment options, as they can often manifest in aggressive disease.

Having demonstrated that selective agonist stimulation of GPR40 produced a strong inhibitory effect on melanoma growth and cell death in culture, the present studies were undertaken to evaluate whether selective GPR40 agonism also induces cell death in neural crest-derived tumors.

Neuroblastoma cell lines used to perform the present studies include: ShSY5Y, IMR-32, SK-NSH, SK-NAS. Melanoma cell lines used include: A2058, A375, and SK-Mel3. Medullary thyroid carcinoma cell line used includes: TT. Malignant peripheral nerve sheath tumor used includes: sNF94.3. Control cell lines used included: human foreskin fibroblast line (Hs27), breast cancer cell lines (MCF-7 and MDA-MB-321), human umbilical vein endothelial cells (HUVEC) and human melanocytes (HMn). ShSY5Y was cultured in MEM/F12 containing 10% heat inactivated fetal bovine serum (FBS) (Invitrogen/GIBCO, Grand Island, N.Y.). IMR-32 was cultured in MEM containing 10% FBS (Invitrogen/GIBCO). SK-NSH was cultured in RPMI-1640 containing 10% FBS (Invitrogen/GIBCO). SK-Mel 3 was cultured in McCoy's 5a containing 10% FBS (Invitrogen/GIBCO). TT was cultured in F-12K containing 10% FBS (ATCC, Manassas, Va.). MDA-MB-321 was cultured in Leibovitz's L-15 containing 10% FBS (ATCC). HUVEC was cultured with EGM-2 Bullet Kit (Lonza, Hopkinton, Mass.). HMn were cultured in MGM-4 (Lonza). All other cell lines were cultured in DMEM with 10% FBS (Invitrogen/GIBCO). Cells were incubated at 37° C. in a humidified atmosphere with 5% $CO_2$. Cells were plated in 96-well plates to approximately 50% confluence prior to initial treatment.

Cells treated with the GPR40 agonist DHA had growth media that was replaced with each respective media containing 1% FBS and 0.1% FA-free BSA with varying concentrations of DHA (Cayman Chemical, Ann Arbor, Mich.) ranging from 0-250 μM solubilized in ethanol (Pharmco-Aaper, Brookfield, Conn.). Cells treated with the GPR40 agonist TAK-875 had growth media that was replaced with each respective media containing 10% FBS with varying concentration of TAK-875 (Selleck Chemicals, Houston, Tex.) ranging from 0-0.4 μM solubilized in dimethyl sulfoxide (Sigma-Aldrich, St. Louis, Mo.). Following 72 hours (TAK-875) or 144 hours (DHA) of treatment, viable cells were quantified using an absorbance-based cell viability assay (Cell Counting Kit-8, Dojindo, Kumamoto, Japan).

Figure 5:
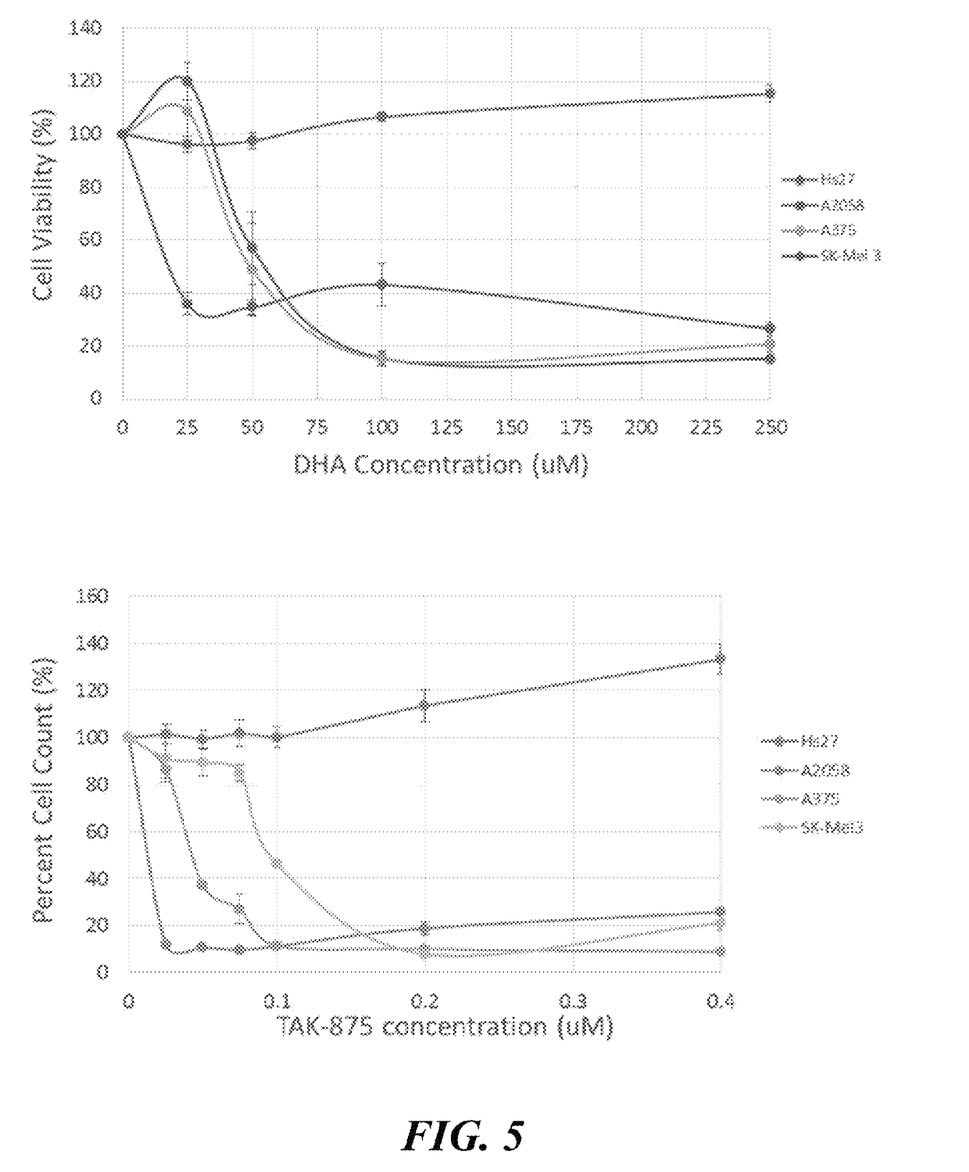
FIG. 5 depicts the effects that exposure to the GPR40 agonists DHA and TAK-875 for 6 days had on human melanoma cell lines (A2058, A375, SK-Mel 3) and on a control human foreskin fibroblast (Hs27) cell line. All 3 human melanoma cell lines exhibited a significant decrease in cell viability following exposure to the GPR40 agonists DHA (top) and TAK-875 (bottom), while little effect was observed on the control Hs27 cell line with either agent.
Figure 6:
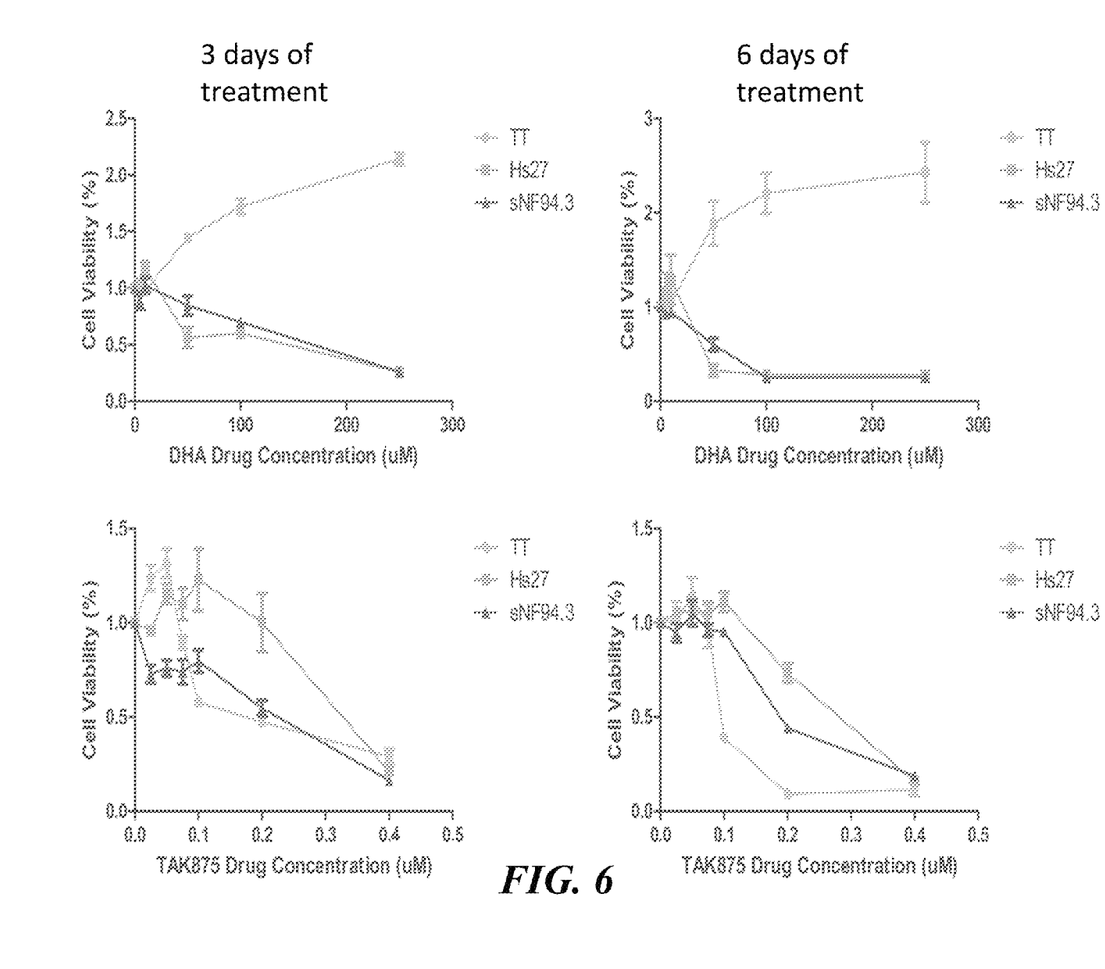
FIG. 6 shows the effects that exposure to the GPR40 agonists DHA and TAK-875 for 3 and 6 days had on the human medullary thyroid carcinoma cell line (TT) and the malignant peripheral nerve sheath tumor (MPNST) (sNF94.3) cell line relative to a control human foreskin fibroblast (Hs27) cell line. The cell viability of the human medullary thyroid carcinoma cell line (TT) was promoted with DHA treatment (top), whereas a pronounced decrease was observed with TAK-875 treatment (bottom). A pronounced effect was observed in the MPNST (sNF94.3) cell line following exposure to DHA and TAK-875. Toxicity was observed in the control Hs27 cell line at high concentrations of both DHA and TAK-875.

As illustrated in FIG. 6, DHA exhibited a minimal inhibitory affect against the medullary thyroid carcinoma cell line (top). However, as illustrated in FIGS. 4-6 cell death was observed in neuroblastoma, melanoma, MPNST, and fibroblasts at high DHA concentrations.

Figure 4:
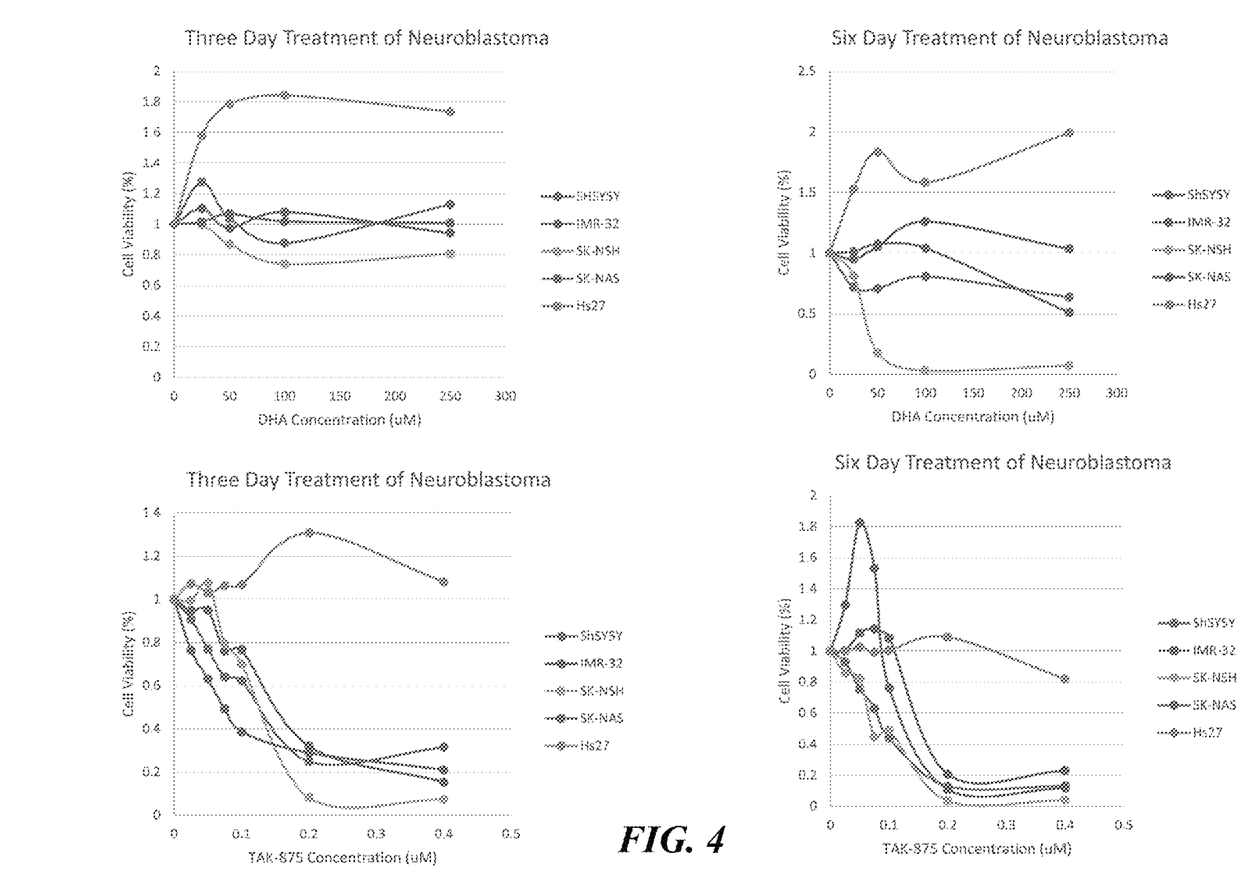
FIG. 4 illustrates the effects that exposure to the GPR40 agonists DHA and TAK-875 for 3 and 6 days had on neuroblastoma cell lines (ShSY5Y, IMR-32, SF-NSF, SK-NAS) and on a control human foreskin fibroblast (Hs27) cell line. A significant decrease in SK-NSH cell viability was observed following treatment with DHA (top), however, all cell lines had significantly attenuated viability following treatment with TAK-875 (bottom). Little to no effect was observed on the control Hs27 cell line with either agent.
Figure 7:
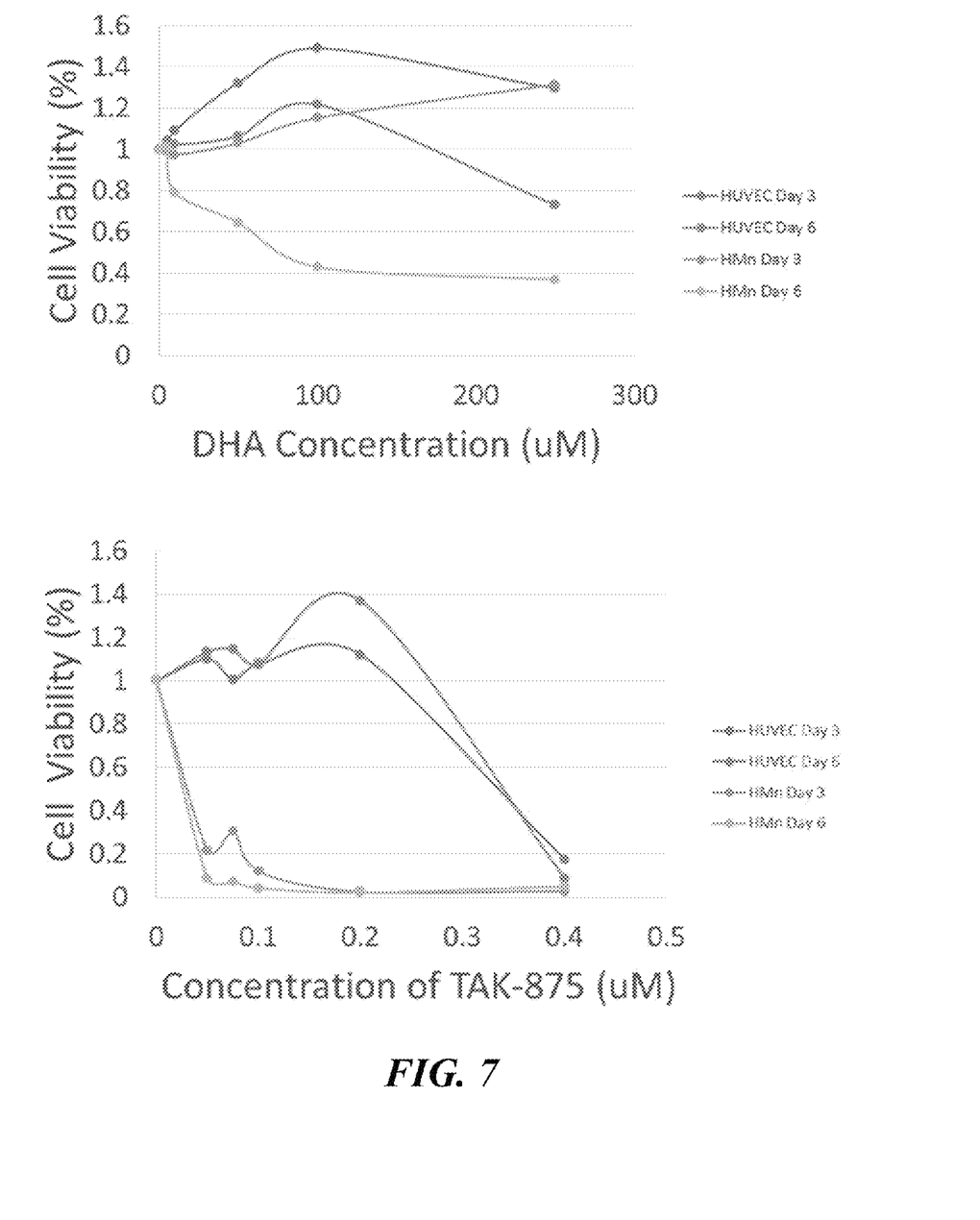
FIG. 7 illustrates the effects that exposure to the GPR40 agonists DHA and TAK-875 for 3 and 6 days had on human umbilical vein endothelial cells (HUVEC) and human melanocytes (HMn) to determine if there was any anti-angiogenic pathogenesis in the decrease of cell viability with melanoma, and if these agents were toxic to primary melanocytes. Treatment with TAK-875 was associated with a dramatic decrease in cell viability in the primary melanocytes, whereas a similar effect in cell viability was observed in HUVEC at only very high concentrations.
Figure 8:
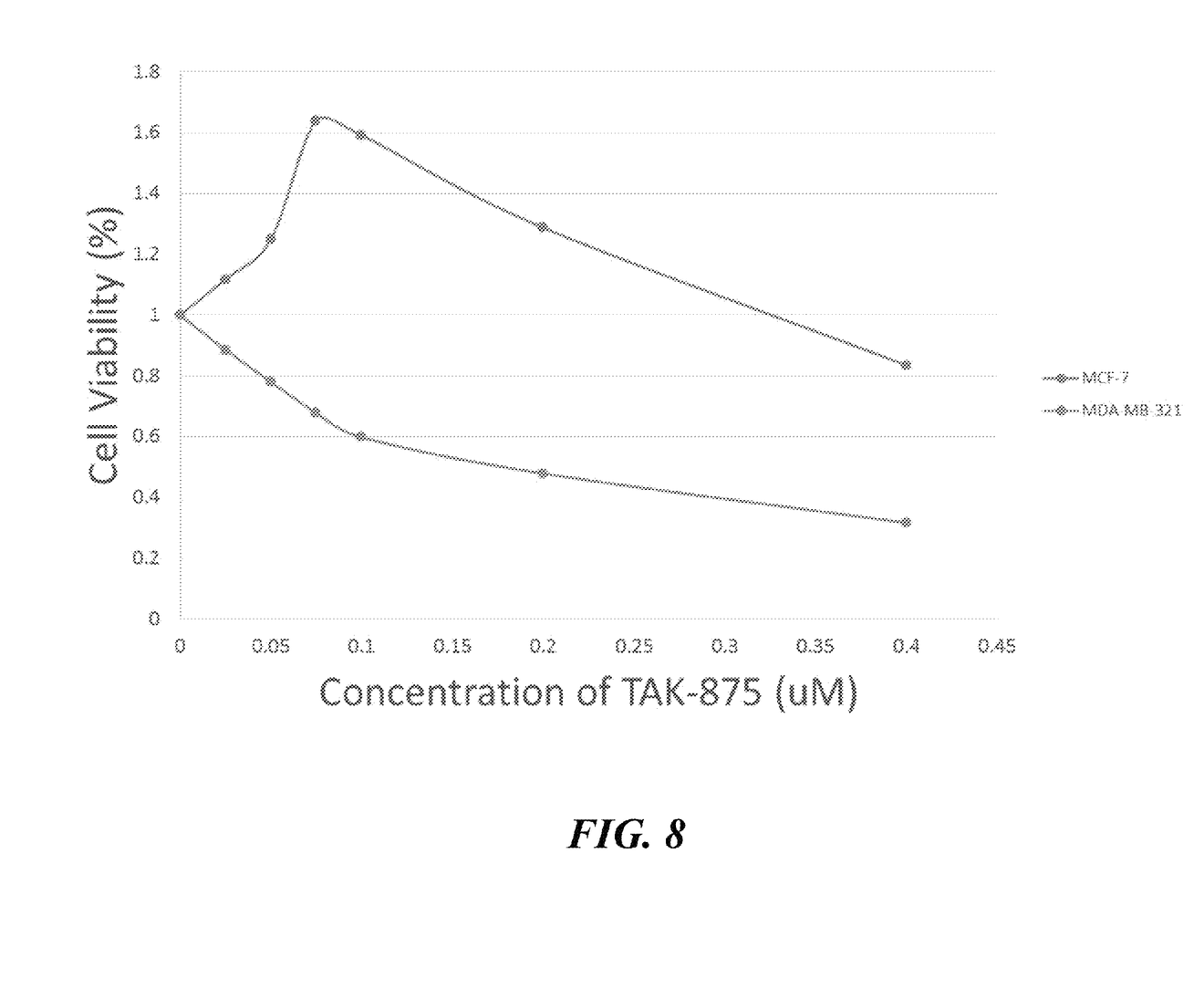
FIG. 8 depicts the effects that exposure to the GPR40 agonist TAK-875 for 6 days had on breast cancer cell lines (MCF-7, MDA-MB-321). Following exposure to TAK-875, a decrease in cell viability was observed at high concentrations.

TAK-875 also produced a profound selective inhibitory effect on cell growth and promoted cell death of all of the neural crest-derived tumor cell lines without toxicity in the control fibroblast line at nanomolar concentrations, as illustrated in FIGS. 4-6. Moreover, primary melanocytes exhibited similar sensitivity following exposure to DHA and TAK-875, as shown in FIG. 7. As also depicted in FIG. 7, there appears to be no relationship to anti-angiogenesis, as the endothelial line showed minimal change in viability with treatment. These observations appear to be a neural crest-specific response, as human breast cancer cell lines exhibited little change in cell viability following exposure to TAK-875 except at the highest tested concentrations (FIG. 8). The foregoing results thus demonstrate that selective GPR40 agonism appears to produce cell death specifically in neural crest-derived tumors.

Discussion

The shift in human dietary habits over the last 100 years toward a very high omega-6 to omega-3 FA ratio is accompanied by a rising incidence of malignant melanoma, and based on such knowledge the present inventors sought to determine the impact of a diet rich in omega-3 fatty acids on the growth of human melanoma. The foregoing studies demonstrate that the omega-3 fatty acid docosahexaenoic acid (DHA) has a profound inhibitory effect on the growth of human melanoma cells in vitro and, for the first time, demonstrate that the growth of human melanoma in vivo is also inhibited by a diet rich in DHA and that such inhibitory effects are mediated by GPR40.

The foregoing studies evidence that a specific G-protein coupled receptor, GPR40, is expressed at high levels in several human melanoma cell lines while being expressed at very low to negligible levels in a control fibroblast cell line, in human neuroblastoma cell lines and in breast cancer cell lines. Moreover, the present studies provide evidence that stimulating GPR40 has a profound inhibitory effect on the growth of human melanoma cells both in vitro, as well as on established human melanoma tumors in vivo. Thus, the present inventors propose GPR40 as a new therapeutic target for the treatment of cancers such as melanoma (e.g., human melanoma).

The field of omega-3 fatty acid research may be in its infancy, but it is becoming increasingly clear that these fats have certain beneficial effects on human health. It is unfortunate that parallel with our improved understanding of the beneficial health effects of omega-3 fatty acids there has been an increasing trend towards the consumption of a diet rich in omega-6 fatty acids and relatively deplete in omega-3 fatty acids. This change is particularly relevant to melanoma, given that the shift in dietary habits over the last 100 years is accompanied by an upward trend in incidence of melanoma, with this rate now equating to the fastest rate of rise in the incidence of any cancer worldwide.

To our knowledge the foregoing represents the first studies to evaluate the effect of dietary omega-3 fatty acids on the growth of a human melanoma cell line in vivo. Although the data on the beneficial health effects of omega-3 fatty acids is mounting, our understanding of the mechanisms via which these molecules exert their effects remains relatively undeveloped. Various molecular mechanisms have been proposed with different levels of evidence, including alterations in arachiodonic acid oxidative metabolism and metabolic conversion of omega-3 fatty acids to bioreactive derivatives, modification of oxidative stress and changes in membrane fluidity and structure (Calviello, G., et al. Nutr Cancer 61: 287-301 (2009)). The recent implication of GPR120 for the first time described a receptor via which these effects may be mediated (Oh, D., at al. Cell 142: 687-698 (2010)).

Herein, the present inventors have demonstrated that GPR40 is expressed at a higher level by human melanoma cells compared to control fibroblast cells and other malignancies. Furthermore, the present inventors have demonstrated that once daily treatment with the orally bioavailable GPR40 receptor specific agonist, TAK-875, significantly inhibited the growth of established human melanoma tumors in vivo. The fact that TAK-875 has been shown to be safe and well tolerated at very high doses by rats and healthy human subjects without significant side-effects makes the potential of using this drug in the treatment of metastatic melanoma especially exciting. Previous reports demonstrate that this receptor is not expressed in the vast majority of normal tissues (Itoh, Y., at al. Nature 422: 173-176 (2003)) thus, stimulating this receptor, would in theory, not have any detrimental effects on these normal tissues. The dose used in the current study is the mouse equivalent of the dose previously used and reported to be safe in rat studies (Tsujihata, Y., et al., J Pharmacol Exp Ther 339: 228-237 (2011)).

In summary, the present inventors have demonstrated that DHA has a profound and selective inhibitory effect on the growth of human melanoma cells in vitro and for the first time used a murine model of human melanoma to demonstrate that dietary DHA inhibits the growth of human melanoma in vivo. In addition, GPR40 has been identified as being expressed at relatively high levels in human melanoma and the present inventors demonstrate that stimulating this receptor with the selective agonist, TAK-875, inhibits the growth of human melanoma cells in vitro and in established tumors in vivo. Given the oral bioavailability and the already confirmed favorable safety profile of TAK-875, we identify GPR40 as a novel, safe and potentially effective therapeutic target for the treatment of human melanoma.

What is claimed is:

1. A method of treating melanoma in a subject affected by melanoma, wherein the method comprises administering a composition to the subject and thereby treating the melanoma, wherein the composition comprises an effective amount of a G-protein coupled receptor 40 (GPR40) agonist; and wherein the GPR40 agonist is not an omega-3 fatty acid, an omega-6 fatty acid, or compound C.

2. The method of claim 1, wherein the G-protein coupled receptor 40 (GPR40) agonist comprises TAK-875 or a pharmaceutically acceptable salt thereof.

3. The method of claim 1, wherein the G-protein coupled receptor 40 (GPR40) agonist is selected from the group consisting of GW9508, TAK-875, AMG-837, TUG-469, compound 4p, and pharmaceutically acceptable salts thereof.

4. The method of claim 1, wherein the method further comprises administering an effective amount of one or more chemotherapeutic agents to the subject.

5. The method of claim 1, wherein the subject is a mammal.

6. The method of claim 1, wherein the subject is a human.

7. The method of claim 1, wherein the composition is administered orally, subcutaneously, topically, or intravenously to the subject.

* * * * *